(12) United States Patent
Schaack et al.

(10) Patent No.: US 8,106,179 B2
(45) Date of Patent: Jan. 31, 2012

(54) SMALL INTERFERING RNA SPECIFIC TO SUB-UNITS α, α' AND β OF THE KINASE PROTEIN CK2, AND THE APPLICATIONS OF THE SAME

(75) Inventors: Béatrice Schaack, Grenoble (FR); Claude Cochet, Claix (FR); Odile Filhol-Cochet, Claix (FR); Brigitte Fouque, Seyssinet Pariset (FR)

(73) Assignees: Commissariat a l'Energie Atomique, Paris (FR); Institut National de la Sante et de la Recherche Medicale, Paris (FR)

( * ) Notice: Subject to any disclaimer, the term of this patent is extended or adjusted under 35 U.S.C. 154(b) by 189 days.

(21) Appl. No.: 10/563,011

(22) PCT Filed: Jul. 2, 2004

(86) PCT No.: PCT/FR2004/001729
§ 371 (c)(1),
(2), (4) Date: Jun. 19, 2006

(87) PCT Pub. No.: WO2005/005632
PCT Pub. Date: Jan. 20, 2005

(65) Prior Publication Data
US 2007/0219148 A1    Sep. 20, 2007

(30) Foreign Application Priority Data
Jul. 2, 2003    (FR) .................................... 03 08032

(51) Int. Cl.
*C07H 21/04*    (2006.01)
(52) U.S. Cl. ..................................................... 536/24.5
(58) Field of Classification Search ................... 536/24.5
See application file for complete search history.

(56) References Cited

U.S. PATENT DOCUMENTS

| | | | |
|---|---|---|---|
| 5,624,803 A * | 4/1997 | Noonberg et al. ................. | 435/6 |
| 6,225,054 B1 * | 5/2001 | Frudakis et al. ................... | 435/6 |
| 6,287,866 B1 * | 9/2001 | Mukerji et al. ............... | 435/488 |
| 6,440,738 B1 * | 8/2002 | Wyatt ............................ | 435/325 |
| 6,455,307 B1 | 9/2002 | McKay et al. | |
| 2002/0086356 A1 * | 7/2002 | Tuschl et al. ................. | 435/69.1 |
| 2002/0147163 A1 | 10/2002 | McKay et al. | |
| 2003/0143732 A1 * | 7/2003 | Fosnaugh et al. ............. | 435/325 |
| 2005/0246794 A1 * | 11/2005 | Khvorova et al. ............ | 800/286 |

FOREIGN PATENT DOCUMENTS
WO    00/63364    10/2000

OTHER PUBLICATIONS

Orlandini et al. Journal of Biological Chemistry 1998, vol. 273, pp. 21291-21297.*
Bass Nature 2001, vol. 411, pp. 428-429.*
Tuschl 2001, siRNA user guide.*
Ulloa, Luis et al, "Depletion of Casein Kinase II by Antisense Oligonucleotide Prevents Neuritogenesis in Neuroblastoma Cells", The EMBO Journal, Oxford University Press, vol. 12, No. 4, pp. 1633-1640, 1993.
Faust, Russell A. et al, "Antisense Oligonucleotides Against Protein Kinase CK2-alpha Inhibit Growth of Squamous Cell Carcinoma of the Head and Neck in Vitro", Head & Neck, vol. 22, No. 4, pp. 341-346, Jul. 2000.
Voorhoeve, P. Mathijs et al, "Knockdown stands up", Trends in Biotechnology, vol. 21, No. 1, pp. 2-4, Jan. 2003.
Read, Martin L. et al, "RNA-based therapeutic strategies for cancer", Expert Opinion on Therapeutic Patents, vol. 13, No. 5, pp. 627-638, 2003.
Parrish, Susan et al, "Functional Anatomy of a dsRNA Trigger: Differential Requirement for the Two Trigger Strands in RNA Interference", Molecular Cell, vol. 6, No. 5, pp. 1077-1087, Nov. 2000.
Elbashir, Sayda M. et al, "Functional anatomy of siRNAs for mediating efficient RNAi in *Drosophila melanogaster* embryo lysate", The EMBO Journal, Oxford University Press, vol. 20, No. 23, pp. 6877-6888, 2001.
Brantl, Sabine., "Antisense-RNA regulation and RNA interference", Biochimica et Biophysica Acta, vol. 1575, No. 1-3, pp. 15-25, 2002.
Ahmed, Khalil et al, "Joining the cell survival squad: an emerging role for protein kinase CK2", Trends in Cell Biology, vol. 12, No. 5, pp. 226-230, 2002.
Valero, Emmanuelle et al, "Modulation of the Protein Kinase CK2 Activity by a Synthetic Peptide Corresponding to the N-Terminus of Its beta Regulatory Subunit", Biochemical and Biophysical Research Communictions, vol. 232, No. 1, pp. 178-182, 1997.

* cited by examiner

*Primary Examiner* — Brian Whiteman
(74) *Attorney, Agent, or Firm* — Oblon, Spivak, McClelland, Maier & Neustadt, L.L.P.

(57) ABSTRACT

The invention relates to small interfering RNA specific to sub-units α, α' and β of the kinase protein CK2, and to the applications of the same, especially for treating cancer and viral illnesses.

17 Claims, 4 Drawing Sheets

Figure 1:
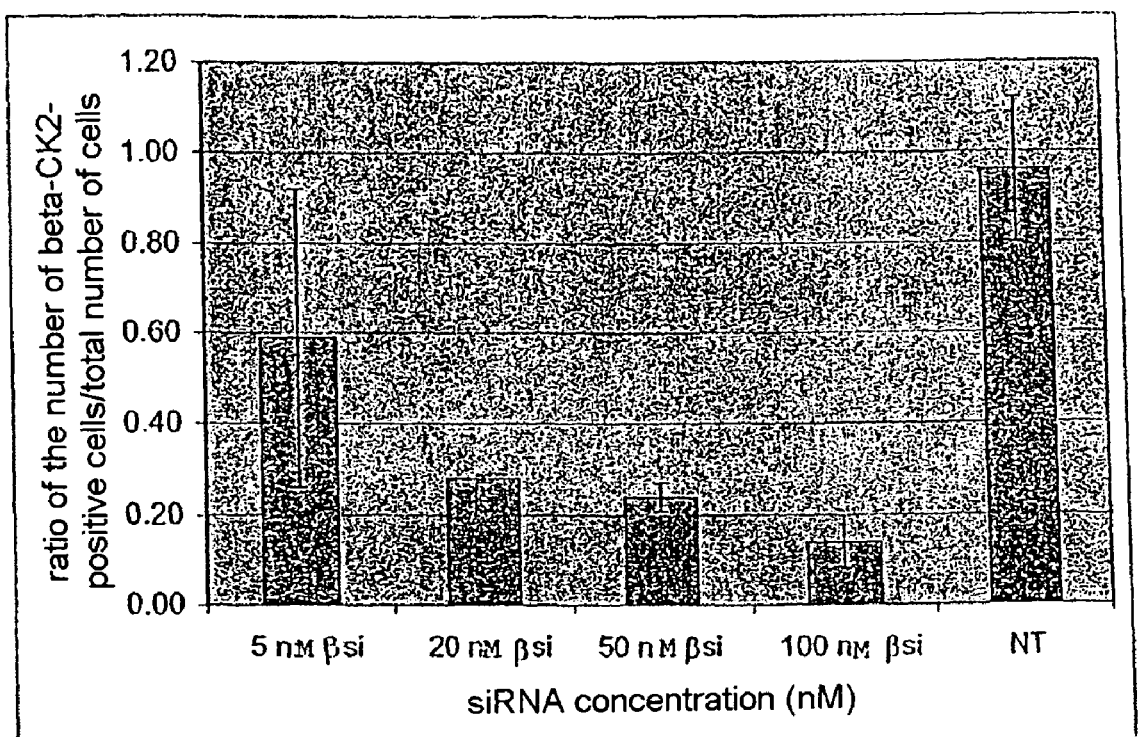

SEQUENCE LISTING

```
<160> NUMBER OF SEQ ID NOS: 133

<210> SEQ ID NO 1
<211> LENGTH: 21
<212> TYPE: DNA
<213> ORGANISM: Mus musculus

<400> SEQUENCE: 1
aagcagggcc agagtttaca c                                              21

<210> SEQ ID NO 2
<211> LENGTH: 21
<212> TYPE: DNA
<213> ORGANISM: Mus musculus

<400> SEQUENCE: 2
aacacacaca gaccccgaga g                                              21

<210> SEQ ID NO 3
<211> LENGTH: 21
<212> TYPE: DNA
<213> ORGANISM: Mus musculus

<400> SEQUENCE: 3
cagaccccga gagtactggg a                                              21

<210> SEQ ID NO 4
<211> LENGTH: 21
```

-continued

```
<212> TYPE: DNA
<213> ORGANISM: Mus musculus

<400> SEQUENCE: 4
aatttgagag gtgggcccaa c                                              21

<210> SEQ ID NO 5
<211> LENGTH: 21
<212> TYPE: DNA
<213> ORGANISM: Mus musculus

<400> SEQUENCE: 5
aatgtccgag ttgcttctcg a                                              21

<210> SEQ ID NO 6
<211> LENGTH: 21
<212> TYPE: DNA
<213> ORGANISM: Mus musculus

<400> SEQUENCE: 6
tgtggagctt gggttgtatg c                                              21

<210> SEQ ID NO 7
<211> LENGTH: 20
<212> TYPE: DNA
<213> ORGANISM: Mus musculus

<400> SEQUENCE: 7
tcagttggtg aggatagcca                                                20

<210> SEQ ID NO 8
<211> LENGTH: 21
<212> TYPE: DNA
<213> ORGANISM: Mus musculus

<400> SEQUENCE: 8
tggtgaggat agccaaggtt c                                              21

<210> SEQ ID NO 9
<211> LENGTH: 19
<212> TYPE: DNA
<213> ORGANISM: Mus musculus

<400> SEQUENCE: 9
aggatagcca aggttctgg                                                 19

<210> SEQ ID NO 10
<211> LENGTH: 21
<212> TYPE: DNA
<213> ORGANISM: Mus musculus

<400> SEQUENCE: 10
aacgatatct tgggcagaca c                                              21

<210> SEQ ID NO 11
<211> LENGTH: 21
<212> TYPE: DNA
<213> ORGANISM: Mus musculus

<400> SEQUENCE: 11
gatatcttgg gcagacactc c                                              21

<210> SEQ ID NO 12
<211> LENGTH: 21
```

```
<212> TYPE: DNA
<213> ORGANISM: Mus musculus

<400> SEQUENCE: 12
aaaaccagca tcttgtcagc c                                             21

<210> SEQ ID NO 13
<211> LENGTH: 21
<212> TYPE: DNA
<213> ORGANISM: Mus musculus

<400> SEQUENCE: 13
aaccagcatc ttgtcagccc t                                             21

<210> SEQ ID NO 14
<211> LENGTH: 21
<212> TYPE: DNA
<213> ORGANISM: Homo sapiens

<400> SEQUENCE: 14
aacagtctga ggagccgcga g                                             21

<210> SEQ ID NO 15
<211> LENGTH: 21
<212> TYPE: DNA
<213> ORGANISM: Homo sapiens

<400> SEQUENCE: 15
aaaacttggt cggggcaagt a                                             21

<210> SEQ ID NO 16
<211> LENGTH: 21
<212> TYPE: DNA
<213> ORGANISM: Homo sapiens

<400> SEQUENCE: 16
aaaggaccct gtgtcaaaga c                                             21

<210> SEQ ID NO 17
<211> LENGTH: 21
<212> TYPE: DNA
<213> ORGANISM: Homo sapiens

<400> SEQUENCE: 17
aagcaactct accagatcct g                                             21

<210> SEQ ID NO 18
<211> LENGTH: 21
<212> TYPE: DNA
<213> ORGANISM: Homo sapiens

<400> SEQUENCE: 18
aaagctctgg attactgcca c                                             21

<210> SEQ ID NO 19
<211> LENGTH: 21
<212> TYPE: DNA
<213> ORGANISM: Homo sapiens

<400> SEQUENCE: 19
aagggaatca tgcacaggga t                                             21

<210> SEQ ID NO 20
<211> LENGTH: 21
```

```
<212> TYPE: DNA
<213> ORGANISM: Homo sapiens

<400> SEQUENCE: 20
aagggaccag agctccttgt g                                              21

<210> SEQ ID NO 21
<211> LENGTH: 21
<212> TYPE: DNA
<213> ORGANISM: Homo sapiens

<400> SEQUENCE: 21
aattgccaag gttctgggga c                                              21

<210> SEQ ID NO 22
<211> LENGTH: 21
<212> TYPE: DNA
<213> ORGANISM: Homo sapiens

<400> SEQUENCE: 22
aacattcacg gaagcgctgg g                                              21

<210> SEQ ID NO 23
<211> LENGTH: 21
<212> TYPE: DNA
<213> ORGANISM: Homo sapiens

<400> SEQUENCE: 23
aacaggcacc ttgtcagccc g                                              21

<210> SEQ ID NO 24
<211> LENGTH: 21
<212> TYPE: DNA
<213> ORGANISM: Homo sapiens

<400> SEQUENCE: 24
aaagaggcca tggagcaccc a                                              21

<210> SEQ ID NO 25
<211> LENGTH: 21
<212> TYPE: DNA
<213> ORGANISM: Homo sapiens

<400> SEQUENCE: 25
aaggagcagt cccagccttg t                                              21

<210> SEQ ID NO 26
<211> LENGTH: 20
<212> TYPE: DNA
<213> ORGANISM: Homo sapiens

<400> SEQUENCE: 26
aagactacat ccaggacaat                                                20

<210> SEQ ID NO 27
<211> LENGTH: 21
<212> TYPE: DNA
<213> ORGANISM: Homo sapiens

<400> SEQUENCE: 27
tcaatgagca ggtccctcac t                                              21

<210> SEQ ID NO 28
<211> LENGTH: 21
```

-continued

```
<212> TYPE: DNA
<213> ORGANISM: Homo sapiens

<400> SEQUENCE: 28
caatgagcag gtccctcact a                                              21

<210> SEQ ID NO 29
<211> LENGTH: 21
<212> TYPE: DNA
<213> ORGANISM: Homo sapiens

<400> SEQUENCE: 29
acctggagcc tgatgaagaa c                                              21

<210> SEQ ID NO 30
<211> LENGTH: 21
<212> TYPE: DNA
<213> ORGANISM: Homo sapiens

<400> SEQUENCE: 30
tggagcctga tgaagaactg g                                              21

<210> SEQ ID NO 31
<211> LENGTH: 21
<212> TYPE: DNA
<213> ORGANISM: Homo sapiens

<400> SEQUENCE: 31
ggagcctgat gaagaactgg a                                              21

<210> SEQ ID NO 32
<211> LENGTH: 21
<212> TYPE: DNA
<213> ORGANISM: Homo sapiens

<400> SEQUENCE: 32
aagacaaccc caaccagagt g                                              21

<210> SEQ ID NO 33
<211> LENGTH: 21
<212> TYPE: DNA
<213> ORGANISM: Homo sapiens

<400> SEQUENCE: 33
cctgtcggac atcccaggtg a                                              21

<210> SEQ ID NO 34
<211> LENGTH: 21
<212> TYPE: DNA
<213> ORGANISM: Homo sapiens

<400> SEQUENCE: 34
aagctctact gccccaagtg c                                              21

<210> SEQ ID NO 35
<211> LENGTH: 21
<212> TYPE: DNA
<213> ORGANISM: Homo sapiens

<400> SEQUENCE: 35
ccaagagacc tgccaaccag t                                              21

<210> SEQ ID NO 36
<211> LENGTH: 21
```

```
<212> TYPE: DNA
<213> ORGANISM: Homo sapiens

<400> SEQUENCE: 36
ccaggctcta cggtttcaag a                                              21

<210> SEQ ID NO 37
<211> LENGTH: 21
<212> TYPE: DNA
<213> ORGANISM: Homo sapiens

<400> SEQUENCE: 37
aagatccatc cgatggccta c                                              21

<210> SEQ ID NO 38
<211> LENGTH: 21
<212> TYPE: DNA
<213> ORGANISM: Homo sapiens

<400> SEQUENCE: 38
agcaacttca agagcccagt c                                              21

<210> SEQ ID NO 39
<211> LENGTH: 21
<212> TYPE: DNA
<213> ORGANISM: Homo sapiens

<400> SEQUENCE: 39
aacttcaaga gcccagtcaa g                                              21

<210> SEQ ID NO 40
<211> LENGTH: 21
<212> TYPE: DNA
<213> ORGANISM: Homo sapiens

<400> SEQUENCE: 40
agagcccagt caagacgatt c                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 41
gcagggccag aguuuacact t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 42
cacacacaga ccccgagagt t                                              21
```

```
<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 43
aauacacaca gaccucgagt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 44
gaccccgaga guacugggat t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 45
uuugagaggu gggcccaact t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 46
uguccgaguu gcuucucgat t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 47
uggagcuugg guuguaugct t                                              21
```

```
<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 48
caguugguga ggauagccat t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 49
gugaggauag ccaagguuct t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 50
aggauagcca agguucuggt t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 51
cgauaucuug ggcagacact t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 52
uaucuugggc agacacucct t                                              21
```

```
<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 53
aaccagcacc uugucagcct t                                                   21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 54
ccagcaccuu gucagcccut t                                                   21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 55
cagccugagg agccgcgagt t                                                   21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 56
aacuuggucg gggcaaguat t                                                   21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 57
aggacccugu gucaaagact t                                                   21
```

```
<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 58
gcaacucuac cagauccugt t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 59
agcucuggau uacugccact t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 60
gggaaucaug cacagggaut t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 61
gggaccagag cuccuugugt t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 62
uugccaaggu ucuggggact t                                              21
```

```
<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 63
cauucacgga agcgcugggt t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 64
caggcaccuu gucagcccgt t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 65
agaggccaug gagcacccat t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 66
ggagcagucc cagccuugut t                                              21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 67
gacuacaucc aggacaautt                                                20
```

-continued

```
<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 68
aaugagcagg ucccucacu                                                    19

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 69
caaugagcag gucccucacu a                                                 21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 70
accuggagcc ugaugaagaa c                                                 21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 71
uggagccuga ugaagaacug g                                                 21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 72
ggagccugau gaagaacugg a                                                 21
```

```
<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 73
aagacaaccc caaccagagu g                                            21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 74
ccugucggac aucccaggug a                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 75
gcucuacugc cccaagugct t                                            21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 76
ccaagagacc ugccaaccag u                                            21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 77
ccaggctcta cggtttcaag a                                            21
```

```
<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 78
gauccauccg auggccuact t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 79
agcaacuuca agagcccagu c                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 80
aacttcaaga gcccagtcaa g                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 81
agagcccagt caagacgatt c                                              21

<210> SEQ ID NO 82
<211> LENGTH: 64
<212> TYPE: DNA
<213> ORGANISM: Artificial Sequence
<220> FEATURE:
<223> OTHER INFORMATION: Description of Artificial Sequence: Synthetic
      siRNA sense strand

<400> SEQUENCE: 82
gatcccctga agactacatc caggacttca agagagtcct ggatgtagtc ttcatttttg    60
gaaa                                                                 64

<210> SEQ ID NO 83
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 83
aagacuacau ccaggacaat t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand

<400> SEQUENCE: 84
uuguccugga uguagucuut t                                              21

<210> SEQ ID NO 85
<211> LENGTH: 50
<212> TYPE: RNA
<213> ORGANISM: Artificial Sequence
<220> FEATURE:
<223> OTHER INFORMATION: Description of Artificial Sequence: Synthetic
      hairpin RNA

<400> SEQUENCE: 85
ugaagacuac auccaggacu ucaagagaag uccuggaugu agucuucauu               50

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand

<400> SEQUENCE: 86
ugaagacuac auccaggacu u                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand

<400> SEQUENCE: 87
guccuggaug uagucuucau u                                              21

<210> SEQ ID NO 88
<211> LENGTH: 2323
<212> TYPE: DNA
<213> ORGANISM: Homo sapiens
```

<400> SEQUENCE: 88

```
cccgcctcct ggtaggaggg ggtttccgct tccggcagca gcggctgcag cctcgctctg      60
gtccctgcgg ctggcggccg agccgtgtgt ctcctcctcc atcgccgcca tattgtctgt     120
gtgagcagag gggagagcgg ccgccgccgc tgccgcttcc accacagttt gaagaaaaca     180
ggtctgaaac aaggtcttac ccccagctgc ttctgaacac agtgactgcc agatctccaa     240
acatcaagtc cagctttgtc cgccaacctg tctgacatgt cgggacccgt gccaagcagg     300
gccagagttt acacagatgt aatacacac agacctcgag aatactggga ttacgagtca     360
catgtggtgg aatggggaaa tcaagatgac taccagctgg ttcgaaaatt aggccgaggt     420
aaatacagtg aagtatttga agccatcaac atcacaaata tgaaaaagt tgttgttaaa      480
attctcaagc cagtaaaaaa gaagaaaatt aagcgtgaaa taagatttt ggagaatttg      540
agaggaggtc ccaacatcat cacactggca gacattgtaa aagaccctgt gtcacgaacc     600
cccgccttgg ttttgaaca cgtaaacaac acagacttca gcaattgta ccagacgtta       660
acagactatg atattcgatt ttacatgtat gagattctga aggccctgga ttattgtcac     720
agcatgggaa ttatgcacag agatgtcaag ccccataatg tcatgattga tcatgagcac     780
agaaagctac gactaataga ctggggtttg gctgagtttt atcatcctgg ccaagaatat     840
aatgtccgag ttgcttcccg atacttcaaa ggtcctgagc tacttgtaga ctatcagatg     900
tacgattata gtttggatat gtggagtttg ggttgtatgc tggcaagtat gatctttcgg     960
aaggagccat ttttccatgg acatgacaat tatgatcagt tggtgaggat agccaaggtt    1020
ctggggacag aagatttata tgactatatt gacaaataca cattgaatt agatccacgt     1080
ttcaatgata tcttgggcag acactctcga aagcgatggg aacgctttgt ccacagtgaa    1140
aatcagcacc ttgtcagccc tgaggccttg gatttcctgg acaaactgct gcgatatgac    1200
caccagtcac ggcttactgc aagagaggca atggagcacc cctatttcta cactgttgtg    1260
aaggaccagg ctcgaatggg ttcatctagc atgccagggg gcagtacgcc cgtcagcagc    1320
gccaatatga tgtcagggat ttcttcagtg ccaaccccct tccccttgg acctctggca    1380
ggctcaccag tgattgctgc tgccaacccc cttgggatgc ctgttccagc tgccgctggc    1440
gctcagcagt aacggcccta tctgtctcct gatgcctgag cagaggtggg ggagtccacc    1500
ctctccttga tgcagcttgc gcctggcggg gagggtgaa acacttcaga agcaccgtgt     1560
ctgaaccgtt gcttgtggat ttatagtagt tcagtcataa aaaaaaaatt ataataggct    1620
gattttcttt tttctttttt tttttaactc gaacttttca taactcaggg gattccctga    1680
aaaattacct gcaggtggaa tatttcatgg acaaattttt ttttctcccc tcccaaattt    1740
agttcctcat cacaaaagaa caaagataaa ccagcctcaa tcccggctgc tgcatttagg    1800
tggagacttc ttcccattcc caccattgtt cctccaccgt cccacacttt agggggttgg    1860
tatctcgtgc tcttctccag agattacaaa aatgtagctt tcaggggag gcaggaagaa     1920
aggaaggaag gaaagaagga agggaggacc caatctatag gagcagtgga ctgcttgctg    1980
gtcgcttaca tcactttact ccataagcgc ttcagtgggg ttatcctagt ggctcttgtg    2040
gaagtgtgtc ttagttacat caagatgttg aaaatctacc caaatgcag acagatacta     2100
aaacttctg ttcagtaaga atcatgtctt actgatctaa ccctaaatcc aactcattta     2160
tacttttatt tttagttcag tttaaaatgt tgatacccttc cctcccaggc tccttacctt    2220
ggtcttttcc ctgttcatct cccaacatgc tgtgctccat agctggtagg agagggaagg    2280
caaaatcttt cttagttttc tttgtcttgg ccattttgaa ttc                      2323
```

<210> SEQ ID NO 89
<211> LENGTH: 1677
<212> TYPE: DNA
<213> ORGANISM: Homo sapiens

<400> SEQUENCE: 89

| | | | | | |
|---|---|---|---|---|---|
| tgtcacccag | gctggagtgc | agtggcgcaa | tctcagctca | ctgcaacctc | cacctccctg | 60 |
| gttcaagcga | ttctcctgcc | tcctccgccc | gacgccccgc | gtcccccgcc | gcgccgccgc | 120 |
| cgccaccctc | tgcgcccccgc | gccgcccccc | ggtcccgccc | gccatgcccg | gcccggccgc | 180 |
| gggcagcagg | gcccgggtct | acgccgaggt | gaacagtctg | aggagccgcg | agtactggga | 240 |
| ctacgaggct | cacgtcccga | gctggggtaa | tcaagatgat | taccaactgg | ttcgaaaact | 300 |
| tggtcgggga | aaatatagtg | aagtatttga | ggccattaat | atcaccaaca | atgagagagt | 360 |
| ggttgtaaaa | atcctgaagc | cagtgaagaa | aaagaagata | aaacgagagg | ttaagattct | 420 |
| ggagaacctt | cgtggtggaa | caaatatcat | taagctgatt | gacactgtaa | aggacccccgt | 480 |
| gtcaaagaca | ccagctttgg | tatttgaata | tatcaataat | acagatttta | agcaactcta | 540 |
| ccagatcctg | acagactttg | tatccggtt | ttatatgtat | gaactactta | aagctctgga | 600 |
| ttactgccac | agcaagggaa | tcatgcacag | ggatgtgaaa | cctcacaatg | tcatgataga | 660 |
| tcaccaacag | aaaaagctgc | gactgataga | ttggggtctg | gcagaattct | atcatcctgc | 720 |
| tcaggagtac | aatgttcgtg | tagcctcaag | gtacttcaag | ggaccagagc | tcctcgtgga | 780 |
| ctatcagatg | tatgattata | gcttggacat | gtggagtttg | ggctgtatgt | tagcaagcat | 840 |
| gatctttcga | agggaaccat | tcttccatgg | acaggacaac | tatgaccagc | ttgttcgcat | 900 |
| tgccaaggtt | ctgggtacag | aagaactgta | tgggtatctg | aagaagtatc | acatagacct | 960 |
| agatccacac | ttcaacgata | tcctgggaca | acattcacgg | aaacgctggg | aaaactttat | 1020 |
| ccatagtgag | aacagacacc | ttgtcagccc | tgaggcccta | gatcttctgg | acaaacttct | 1080 |
| gcgatacgac | catcaacaga | gactgactgc | caaagaggcc | atggagcacc | catacttcta | 1140 |
| ccctgtggtg | aaggagcagt | cccagccttg | tgcagacaat | gctgtgcttt | ccagtggtct | 1200 |
| cacggcagca | cgatgaagac | tggaaagcga | cgggtctgtt | gcggttctcc | cacttttcca | 1260 |
| taagcagaac | aagaaccaaa | tcaaacgtct | taacgcgtat | agagagatca | cgttccgtga | 1320 |
| gcagacacaa | aacggtggca | ggtttggcga | gcacgaacta | gaccaagcga | agggcagccc | 1380 |
| accaccgtat | atcaaacctc | acttccgaat | gtaaaaggct | cacttgcctt | tggcttcctg | 1440 |
| ttgacttctt | cccgacccag | aaagcatggg | gaatgtgaag | ggtatgcaga | atgttgttgg | 1500 |
| ttactgttgc | tccccgagcc | cctcaactcg | tcccgtggcc | gcctgttttt | ccagcaaacc | 1560 |
| acgctaacta | gctgaccaca | gactccacag | tgggggacg | ggcgcagtat | gtggcatggc | 1620 |
| ggcagttaca | tattattatt | ttaaaagtat | atattattga | ataaaaggtt | ttaaaag | 1677 |

<210> SEQ ID NO 90
<211> LENGTH: 1128
<212> TYPE: DNA
<213> ORGANISM: Homo sapiens

<400> SEQUENCE: 90

| | | | | | |
|---|---|---|---|---|---|
| gcttctcgtt | gtgccccgcc | cgcaagcgcc | ctcctccggg | ccttcgtgac | agccaggtcg | 60 |
| tgcgcgggtc | atcctgggat | tggtagttcg | ctttctctca | tttagccagt | ttctttctct | 120 |
| accggggact | ccgtgtcccg | gcatccaccg | cggcacctga | cccttggcgc | ttgcgtgttg | 180 |
| ccctcttccc | caccctcct | aatttccact | cccccaccc | cacttcgcct | gccgcggtcg | 240 |

-continued

```
ggtccgcggc ctgcgctgta gcggtcgccg ccgttccctg gaagtagcaa cttccctacc    300
ccaccccagt cctggtcccc gtccagccgc tgacgtgaag atgagcagct cagaggaggt    360
gtcctggatt tcctggttct gtgggctccg tggcaatgaa ttcttctgtg aagtggatga    420
agactacatc caggacaaat ttaatcttac tggactcaat gagcaggtcc ctcactaccg    480
acaagctcta gacatgatct tggacctgga gcctgatgaa gaactggaag acaaccccaa    540
ccagagtgac ctgattgagc aggcagccga gatgctttat ggattgatcc acgcccgcta    600
catccttacc aaccgtggca tcgcccagat gttggaaaag taccagcaag gagactttgg    660
ttactgtcct cgtgtgtact gtgagaacca gccaatgctt cccattggcc tttcagacat    720
cccaggtgaa gccatggtga agctctactg ccccaagtgc atggatgtgt acacacccaa    780
gtcatcaaga caccatcaca cggatggcgc ctacttcggc actggtttcc ctcacatgct    840
cttcatggtg catcccgagt accggcccaa gagacctgcc aaccagtttg tgcccaggct    900
ctacggtttc aagatccatc cgatggccta ccagctgcag ctccaagccg ccagcaactt    960
caagagccca gtcaagacga ttcgctgatt ccctccccca cctgtcctgc agtctttgac   1020
ttttcctttc tttttgcca ccctttcagg aaccctgtat ggtttttagt ttaaattaaa   1080
ggagtcgtta ttgtggtggg aatatgaaat aaagtagaag aaaaggcc              1128
```

```
<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
ucccaguacu cucgggguct t                                               21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
cucgaggucu guguguauut t                                               21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
guguaaacuc uggcccugct t                                               21
```

```
<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
cucucggggu cugugugugt t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
guugggccca ccucucaaat t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
ucgagaagca acucggacat t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
gugucugccc aagauaucgt t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
ggcuagcaag gugcugguut t                                              21
```

```
<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
agggcugaca aggugcuggt t                                           21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
ccaguuccuu ggcuauccut t                                           21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gaaccuuggc uauccucact t                                           21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
uggcuauccu caccaacugt t                                           21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
ggagugucug cccaagauat t                                           21
```

```
<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
gcaucaaacc caagcuccat t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
cucgcggcuc cucaggcugt t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
uacuugcccc gaccaaguut t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
gucuuugaca caggguccut t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
caggaucugg uagaguugct t                                              21
```

```
<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
guggcaguaa uccagagcut t                                          21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
aucccugugc augauuccct t                                          21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
cucaaggagc ucugguccct t                                          21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
guccccagaa ccuuggcaat t                                          21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
cccagcgcuu ccgugaaugt t                                          21
```

```
<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
cgggcugaca aggugccugt t                                                  21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
ugggugcucc auggccucut t                                                  21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
acaaggcugg gacugcucct t                                                  21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cucugguugg gguugucuuc c                                                  21

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
ugagggaccu gcucauuga                                                     19
```

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 119
ucuucaucag gcuccagguc c                                           21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 120
aguucuucau caggcuccag g                                           21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 121
caguucuuca ucaggcucca g                                           21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 122
gugagggacc ugcucauuga g                                           21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 123
ugguuggcag gucucuuggg c                                           21

```
<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
accugggaug uccgacaggc c                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
cugggcucuu gaaguugcug g                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
uugaaaccgu agagccuggg c                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
aucgucuuga cugggctctt g                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
ugacugggcu cuugaaguuc g                                              21
```

```
<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
gcacuugggg caguagagct t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
guaggccauc ggauggauct t                                              21

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
auuguccugg auguaguctt                                                20

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
uuguccugga uguagucuut t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
guccuggaug uagucuucau u                                              21
```

SMALL INTERFERING RNA SPECIFIC TO SUB-UNITS α, α' AND β OF THE KINASE PROTEIN CK2, AND THE APPLICATIONS OF THE SAME

The invention relates to small interfering RNA (or silencing inducing RNA), hereinafter referred to as siRNA, specific for the α, α' and β subunits of the CK2 (or caseine kinase 2) protein kinase and to the applications thereof, in particular for the treatment of cancers.

The CK2 (or caseine kinase 2) protein is a pleiotropic or ubiquitous serine/threonine kinase that is very conserved in eukaryotics; this holoenzyme is composed of two catalytic subunits α and α' and two identical regulatory subunits β, associated in the form of αα'β$_2$, α'$_2$β$_2$ or α$_2$β$_2$ heterotetramers.

This protein plays an essential role in the control of many physiopathological processes; it is essential to embryonic development and to terminal differentiation, and to the control of progression of the cell cycle and of cell survival, and its expression is deregulated in many cancers including tumors of viral origin, where it contributes to the blocking of apoptosis (Buchou et al., Mol. Cell. Biol., 2003, 23, 908-915; Ahmed et al., Trends in Cell Biology, 2002, 12, 226-230).

Because of its essential role in many physiological processes and because of the importance of the pathologies associated with the dysfunction therefor, the CK2 protein represents a new pharmacological target for the development of medicinal products, in particular anticancer and antiviral agents.

However, given that the knocking-out of the CK2 subunit genes is lethal in knock-out transgenic mice and incompatible with cell viability (Buchou et al., mentioned above), the development of such molecules has remained very limited in the absence of any in vivo or in vitro model for the functional analysis of the role of the CK2 subunits.

In fact, the few molecules capable of inhibiting CK2 that have been described have the drawback of being either not very specific or not very active, i.e.:

small molecules which are analogs of ATP, capable of specifically inhibiting the catalytic α and α' subunits; as an ATP analog, mention may be made of TBB (Sarno et al., FEBS lett., 2001, 496, 44-48), which is a derivative of DRB for increasing its specificity for the alpha subunit of CK2. However, these kinase substrate (ATP) analogs can inhibit the activity of other known or unknown proteins, using cellular ATP. Since the specificity of such products, and in particular of TBB, is uncertain, their use is excluded in vivo, antisense oligonucleotides directed against the subunits of CK2 (American application US 2002/147163 and American patent U.S. Pat. No. 6,455,307 in the name of Isis Pharmaceuticals Inc; Ulloa et al., EMBO, 1993, 12, 1633-1640; Faust et al., Head & Neck, 2000, 22, 341-346); the inhibition of CK2 activity, demonstrated only in vitro is partial and transient and requires very high doses of antisense oligonucleotides (several tens to several hundreds μg/ml depending on the sensitivity of the cells).

It emerges from the above that no molecules capable of specifically inhibiting the CK2 protein kinase in an effective manner exists. In addition, no in vitro or in vivo model exists for a functional analysis of each of the CK2 subunits, useful for screening for molecules capable of modulating the activity of the CK2 protein kinase.

It has been shown that double-stranded RNA fragments complementary to an mRNA are capable, where they are introduced into eukaryotic cells, of strongly inhibiting the expression of the corresponding gene by destroying this mRNA. The phenomenon, called RNA interference (for a review see: Biofutur, 2002, volume 228, pages 52-61; Voorhoeve et al., TIBS, 2003, 21, 2-4), has been demonstrated and particularly well studied in plants and invertebrates (*Caenorhabditis elegans*, drosophila) and it is reasonable to assume that a similar mechanism exists in higher animals, since RNA interference has also been observed in human cells in culture. However, it has been shown that, in invertebrates, the phenomenon is even capable of spreading to the entire organism and of persisting after cell division, something which has not been observed in higher animals.

Small double-stranded RNA fragments, 21 to 25 nucleotides long, are the real initiators of the inhibition. These siRNAs can penetrate directly into plant cells and probably also into invertebrate cells. In drosophila, it has been shown that siRNAs integrate into molecular complexes called RISCs (RNA-induced silencing complexes). By means of a helicase and of ATP as an energy source, these complexes expose the strands of the siRNA. If the genetic sequence of the siRNA corresponds to a fragment of a gene that is naturally expressed in the cell, the interfering RNA exposed by the RISC complex will encounter a messenger RNA carrying a sequence that is exactly complementary and the two molecules will associate. The presence of the siRNA strand causes enzymes to become involved which will cleave the messenger RNA at the site where it is bound to the siRNA. The two parts of the cleaved messenger RNA, deprived of one of their usual endings, are identified as incomplete and destroyed by the cell. The messenger RNA targeted can no longer play its role and control the synthesis of a protein. This is what explains the extremely specific nature of RNA interference (R. Agami, Current Opinion in Chemical Biology, 2002, 6, 829-834; there is only a reaction if an exact homolog of the sequence of about twenty nucleotides of the siRNA exists on a messenger RNA. The probability of a segment of DNA, taken randomly, corresponding to a given siRNA is of the order of ¼ to the power 21 (21 nucleotides which can each have 4 "values"), i.e. one chance in more than 4 billion.

This phenomenon of specific inhibition of gene expression opens up advantageous perspectives in the field of functional genomics and of pharmaceutical research, respectively, for rapidly identifying the function of new genes, and for rapidly selecting target genes and candidate medicinal products.

Thus, siRNAs specific for cDNAs encoding viral or cellular proteins and capable of inhibiting the production of the corresponding proteins have been described (p24 of HIV, gD of HSV, IL-12; PCT international application WO 00/63364).

However, no siRNA capable of specifically inhibiting the expression of the subunits of the CK2 protein kinase has been described.

Surprisingly, the inventors have isolated siRNAs specific for the transcripts of the α, α' and β subunits of CK2 that are capable of selectively blocking the expression of the a subunit, of the α' subunit or of the β subunit of the CK2 protein kinase in cells, effectively, specifically and in a long-lasting manner. Such siRNAs which exhibit a prolonged inhibitory effect, of the order of 72 hours, at low concentrations (of the order of 20 nM, in vitro), are useful as medicinal products for the treatment of cancers. Specifically, a concentration of 20 nM of siRNA inhibits more than 80% of the expression of the CK2 protein kinase subunits (detected by Western blotting) and of the corresponding mRNAs (quantification by RT-PCR on a light-cycler) after 48 h in human cells (MCF7, HeLa or 3T3 fibroblasts).

In addition, these RNAs which specifically inhibit the expression of the α, α' or β subunit of the CK2 protein kinase also represents tools for the functional analysis of the respective role of each CK2 unit and the screening for molecules capable of modulating (activating or inhibiting) the activity of one or more of these CK2 subunits.

A subject of the present invention is thus a double-stranded oligonucleotide made up of two strands of 19 to 23 nucleotides, each strand consisting, from 5' to 3', of a sequence of 17 to 21 ribonucleotides and two deoxyribo- or ribonucleotides, the 17 to 21 ribonucleotide RNA sequences of said strands being complementary and the two nucleotides of the 3' ends being protruding, characterized in that the RNA sequence of the sense strand or positive strand is that of a fragment of a transcript of an α, α' or β subunit of a CK2 protein kinase, selected from the group consisting of:

a) a fragment corresponding to an oligonucleotide which inhibits more than 80% of the expression of the corresponding subunit, in cell culture, at a concentration of between 1 and 200 nM, preferably less than 20 nM, b) a fragment of a transcript of an α subunit included between positions 18-74, 259-279, 565-585, 644-664, 720-750, 808-831 and 863-885, from the ATG codon, with reference to the cDNA sequence of the CK2 α subunit of mouse No. NM_007787 or human No. NM_001895, c) a fragment of a transcript of an α' subunit included between positions 49-69, 132-142, 306-326, 367-387, 427-447, 451-471, 595-615, 735-755, 827-847, 868-888, 949-969 and 988-1008, from the ATG codon, with reference to the cDNA sequence of the CK2 α' subunit of mouse NM_009974 or human No. NM_001896, d) a fragment of a transcript of a β subunit included between positions 80-100, 116-127, 164-208, 369-389, 400-420, 527-591 and 613-643, from the ATG codon, with reference to the cDNA sequence of the CK2 β subunit of human No. NM_001320 or of mouse No. NP_034105, and e) a fragment of 17 to 21 nucleotides exhibiting at least 80% identity with the fragments defined in a), b), c) and d).

The double-stranded oligonucleotide according to the invention corresponds to an siRNA capable of inhibiting the expression of the corresponding subunit of the CK2 protein kinase; the 17 to 21 nucleotide RNA sequence of the sense strand or positive strand is that of the target sequence of the transcript of the α, α' or β subunit of the mammalian CK2 protein kinase.

The invention encompasses the natural, synthetic, semisynthetic or recombinant oligonucleotides targeting the CK2 protein kinase of any organism, in particular eukaryotic organism. Given the information provided with reference to the human and mouse sequences, those skilled in the art are in a position to find the equivalent positions in the sequences of other eukaryotic organisms, in particular of mammals, that are accessible in the sequence data bases.

In accordance with the invention, the identity of an oligonucleotide sequence with respect to a reference sequence is assessed as a function of the percentage of nucleotides that are identical, when the sequences are aligned, so as to obtain the maximum correspondence between them.

According to an advantageous embodiment of said double-stranded oligonucleotide, said sequence is selected from the group consisting of:

a) a fragment of an α subunit defined by the RNA equivalent of the sequence SEQ ID Nos: 1 to 13, b) a fragment of an α' subunit defined by the RNA equivalent of the sequence SEQ ID Nos: 14 to 25, c) a fragment of a β subunit defined by the RNA equivalent of the sequence SEQ ID Nos: 26 to 40, and d) a sequence as defined in a), b) or c), truncated by one or two nucleotides at its 5' and/or 3' end.

For the purpose of the present invention, the expression "RNA equivalent of a DNA sequence" is intended to mean the sequence in which the deoxyribonucleotides (a, g, c, t) of said DNA sequence are replaced with the ribonucleotides (a, g, c, u).

According to another advantageous embodiment of said double-stranded oligonucleotide, each of the strands comprises a phosphate group in the 5' position and a hydroxyl group in the 3' position.

According to yet another advantageous embodiment of said double-stranded oligonucleotide, said protruding nucleotides of the 3' ends are selected from the group consisting of the pairs tt and aa.

According to yet another advantageous embodiment of said double-stranded oligonucleotide, it is made up of two strands of 19 or 20 nucleotides.

According to an advantageous arrangement of this embodiment of said double-stranded oligonucleotide, it comprises a sense strand defined by the sequence SEQ ID No. 67 or 68.

According to yet another advantageous embodiment of said double-stranded oligonucleotide, it is made up of two stands of 21 to 23 nucleotides.

According to an advantageous arrangement of this embodiment of said double-stranded oligonucleotide, it comprises a sense strand as defined by the sequence SEQ ID Nos. 41 to 66, 69 to 81, 83 and 86.

Tables I, II and III below summarize the properties of the various oligonucleotides of sequences SEQ ID Nos. 1 to 86.

TABLE I target sequences and SiRNA α

| Name and no. | Mouse target sequence (sense sequence) | SiRNA | Size | Tm | % GC | Position/ATG codon NM_007787 mouse and NM_001895 of the human sequence | Hu*/mouse homology |
|---|---|---|---|---|---|---|---|
| CK2α1 | cagaccccgagagtactggga (SEQ ID NO. 3) | gaccccgagaguacugggatt ttcuggggcucucaugacccu (SEQ ID Nos. 44 & 91, respectively) | 21 | 61.5 | 57 | 54 | 2 |
| CK2α2 | aacacacacagaccccgagag (SEQ ID NO. 2) | aauacacacagaccucgagtt ttuuaugugugucuggagcuc (SEQ ID Nos. 43 & 92, respectively) | 21 | 61.7 | 52.4 | 46 | 2 |

TABLE I-continued target sequences and SiRNA α

| Name and no. | Mouse target sequence (sense sequence) | SiRNA | Size | Tm | % GC | Position/ATG codon NM_007787 mouse and NM_001895 of the human sequence | Hu*/mouse homology |
|---|---|---|---|---|---|---|---|
| CK2α3 | aagcagggccagagtttacac (SEQ ID NO: 1) | gcagggccagaguuuacacuu ttcguccggucucaaaugug (SEQ ID Nos. 41 & 93, respectively) | 21 | 58.6 | 52.4 | 18 | 0 |
| CK2α4 | aacacacacagacccccgagag (SEQ ID NO. 2) | cacacacagaccccgagaguu ttgugugugucuggggcucuc (SEQ ID Nos. 42 & 94, respectively) | 21 | 59.3 | 52.4 | 46 | 2 |
| CK2α5 | aatttgagaggtgggcccaac (SEQ ID NO. 4) | uuugagaggugggcccaacuu ttaaacucuccacccggguug (SEQ ID Nos. 45 & 95, respectively) | 21 | 59.8 | 52.4 | 259 | 2 |
| CK2α6 | aatgtccgagttgcttctcga (SEQ ID NO. 5) | ugugccgaguugcuucucgauu ttacaggcucaacgaagagcu (SEQ ID Nos. 46 & 96, respectively) | 21 | 58.8 | 47.6 | 565 | 1 |
| CK2α7 | aacgatatcttgggcagacac (SEQ ID NO. 10) | cgauaucuugggcagacacuu ttgcuauagaacccgucugug (SEQ ID Nos. 51 & 97, respectively) | 21 | 57.9 | 47.6 | 808 | 1 |
| CK2α8 | aaaaccagcatcttgtcagcc (SEQ ID NO. 12) | aaccagcaccuugucagccuu ttuuggucguggaacgaucgg (SEQ ID Nos. 53 & 98, respectively) | 21 | 60.3 | 47.6 | 863 | 2 |
| CK2α9 | aaccagcatcttgtcagccct (SEQ ID NO. 13) | ccagcaccuugucagcccuuu ttggucguggaacagucggga (SEQ ID Nos. 54 & 99, respectively) | 21 | 62.0 | 52.4 | 865 | 2 |
| CK2α10 | aggatagccaaggttctgg (SEQ ID NO. 9) | aggauagccaagguucugguu ttuccuaucgguuccuugacc (SEQ ID Nos. 50 & 100, respectively) | 21 | 58.9 | 47.6 | 730 | 0 |
| CK2α11 | tggtgaggatagccaaggttc (SEQ ID No. 8) | gugaggauagccaagguucuu ttcacuccuaucgguuccaag (SEQ ID Nos. 49 & 101, respectively) | 21 | 57.1 | 47.6 | 725 | 0 |
| CK2α12 | tcagttggtgaggatagcca (SEQ ID No. 7) | caguuggugaggauagccauu ttgucaaccaccuccuaucggu (SEQ ID Nos. 48 & 102, respectively) | 21 | 58.8 | 47.6 | 720 | 0 |
| CK2α13 | gatatcttgggcagacactcc (SEQ ID No. 11) | uaucuugggcagacacuccuu ttauagaacccgucugugagg (SEQ ID Nos. 52 & 103, respectively) | 21 | 58.6 | 47.6 | 811 | 1 |
| CK2α14 | tgtggagcttgggttgtatgc (SEQ ID No. 6) | uggagcuuggguuguaugcuu ttaccucgaacccaacauacg (SEQ ID Nos. 47 & 104, respectively) | 21 | 61.8 | 47.8 | 644 | 1 |

*Hu = human

NB: the ATG is at position 1 of the mouse sequence No. NM_007787 and in position 277 of the human sequence No. NM_001895.

TABLE II target sequences and SiRNA α'

| Name | Human target sequence (sense sequence) | SiRNA | SIZE | Tm | % GC | Position | Hu/mouse homology |
|---|---|---|---|---|---|---|---|
| CK2α'1 | aacagtctgaggagccgcgag (SEQ ID No. 14) | cagccugaggagccgcgaguu ttgucggacuccucggcgcuc (SEQ ID Nos. 55 & 105, respectively) | 21 | 66.5 | 66.7 | 49 | 1 mismatch |
| CK2α'2 | aaaacttggtcggggcaagta (SEQ ID No. 15) | aacuuggucggggcaaguauu ttuugaaccagccccguucau (SEQ ID Nos. 56 & 106, respectively) | 21 | 59.5 | 47.6 | 132 | 2 mismatches |
| CK2α'3 | aaaggaccctgtgtcaaagac (SEQ ID No. 16) | aggacccugugucaaagacuu ttuccugggacacaguuucug (SEQ ID Nos. 57 & 107, respectively) | 21 | 62.4 | 47.6 | 306 | 1 |
| CK2α'4 | aagcaactctaccagatcctg (SEQ ID No. 17) | gcaacucuaccagauccuguu ttcguugagauggucuaggac (SEQ ID Nos. 58 & 108, respectively) | 21 | 55.8 | 47.6 | 367 | 0 |
| CK2α'5 | aaagctctggattactgccac (SEQ ID No. 18) | agcucuggauuacugccacuu ttucgagaccuaaugacggug (SEQ ID Nos. 59 & 109, respectively) | 21 | 58.2 | 47.6 | 427 | 0 |
| CK2α'6 | aagggaatcatgcacagggat (SEQ ID No. 19) | gggaaucaugcacagggauuu ttcccuuaguacgugucccua (SEQ ID Nos. 60 & 110, respectively) | 21 | 62.8 | 47.6 | 451 | 0 |
| CK2α'7 | aagggaccagagctccttgtg (SEQ ID No. 20) | gggaccagagcuccuugugutt ttcccuggucucgaggaacuc (SEQ ID Nos. 61 & 111, respectively) | 21 | 65.2 | 57.1 | 595 | 1 |
| CK2α'8 | aattgccaaggttctggggac (SEQ ID No. 21) | uugccaagguucuggggacuu ttaacgguccaagacccccug (SEQ ID Nos. 62 & 112, respectively) | 21 | 61.5 | 52.4 | 735 | 2 but at the ends |
| CK2α'9 | aacattcacggaagcgctggg (SEQ ID No. 22) | cauucacggaagcgcugggtt ttguaagugccuucgcgaccc (SEQ ID Nos. 63 & 113, respectively) | 21 | 66.4 | 57.1 | 827 | 1 |
| CK2α'10 | aacaggcaccttgtcagcccg (SEQ ID No. 23) | caggcaccuugucagcccguu ttguccguggaacagucgggc (SEQ ID Nos. 64 & 114, respectively) | 21 | 61.0 | 61.9 | 868 | 2, of which one is the last nt |
| CK2α'11 | aaagaggccatggagcaccca (SEQ ID No. 24) | agaggccauggagcacccauu ttucuccgguaccucguggu (SEQ ID Nos. 65 & 115, respectively) | 21 | 68.4 | 57.1 | 949 | 0 |
| CK2α'12 | aaggagcagtcccagccttgt (SEQ ID No. 25) | ggagcagucccagccuuguu ttccucgucagggucggaaca (SEQ ID Nos. 66 & 116, respectively) | 21 | 64.6 | 57.1 | 988 | 0 |

NB: The ATG is at position 99 of the mouse sequence No. NM_009974 and at position 164 of the human sequence No. NM_001896.

TABLE III target sequences and SiRNA β

| Name | Human target sequence (sense sequence) | SiRNA | Size | Tm | % GC | Position | Hu/mouse homology |
|---|---|---|---|---|---|---|---|
| CK2β1 | aagacaaccccaaccagagtg (SEQ ID No. 32) | aagacaaccccaaccagagug ccuucuguggggguugucuc (SEQ ID Nos. 73 & 117, respectively) | 21 | 61.2 | 52.4 | 188 | 0 mismatch |

TABLE III-continued target sequences and SiRNA β

| Name | Human target sequence (sense sequence) | SiRNA | Size | Tm | % GC | Position | Hu/mouse homology |
|---|---|---|---|---|---|---|---|
| CK2β2 | tcaatgagcaggtccctcact (SEQ ID No. 27) | aaugagcaggucccucacu aguuacucguccagggagu (SEQ ID Nos. 68 & 118, respectively) | 19 | 62 | 52.4 | 116 | 0 |
| CK2β3 | acctggagcctgatgaagaac (SEQ ID No. 29) | accuggagccugaugaagaac ccuggaccucggacuacuucu (SEQ ID Nos. 70 & 119, respectively) | 21 | 60.5 | 52.4 | 164 | 1 |
| CK2β4 | tggagcctgatgaagaactgg (SEQ ID No. 30) | uggagccugaugaagaacugg ggaccucggacuacuucuuga (SEQ ID Nos. 71 & 120, respectively) | 21 | 62.5 | 52.3 | 167 | 1 |
| CK2β5 | ggagcctgatgaagaactgga (SEQ ID No. 31) | ggagccugaugaagaacugga gaccucggacuacuucuugac (SEQ ID Nos. 72 & 121, respectively) | 21 | 62.5 | 52.3 | 168 | 1 |
| CK2β6 | caatgagcaggtccctcacta (SEQ ID No. 28) | caaugagcaggucccucacua gaguuacucguccagggagug (SEQ ID Nos. 69 & 122, respectively) | 21 | 60.1 | 52.3 | 117* | 0 |
| CK2β7 | ccaagagacctgccaaccagt (SEQ ID No. 35) | ccaagagaccugccaaccagu cgguuucucuggacgguuggu (SEQ ID Nos. 76 & 123, respectively) | 21 | 62 | 47.6 | 527 | 1 |
| CK2β8 | cctgtcggacatcccaggtga (SEQ ID No. 33) | ccugucggacaucccagguga ccggacagccuguagggucca (SEQ ID Nos. 74 & 124, respectively) | 21 | 62.2 | 52.3 | 369 | 3 |
| CK2β9 | agcaacttcaagagcccagtc (SEQ ID No. 38) | agcaacuucaagagcccaguc ggucguugaaguucucgdggguc (SEQ ID Nos. 79 & 125, respectively) | 21 | 60.8 | 52.3 | 613 | 0 |
| CK2β10 | ccaggctctacggttttcaaga (SEQ ID No. 36) | ccaggcucuacggguuucaaga cgggguccgagaugccaaaguu (SEQ ID Nos. 77 & 126, respectively) | 21 | 60.5 | 52.3 | 554 | 1 |
| CK2β11 | agagcccagtcaagacgattc (SEQ ID No. 40) | agagcccagucaagacgauuc guucucgggucaguucugcua (SEQ ID Nos. 81 & 127, respectively) | 21 | 60.6 | 52.3 | 623 | 0 |
| CK2β12 | aacttcaagagcccagtcaag (SEQ ID No. 39) | aacuucaagagcccagucaag gcuugaaguucucgggucagu (SEQ ID Nos. 80 & 128, respectively) | 21 | 60.8 | 52.3 | 616 | 0 |
| CK2β13 | aagctctactgccccaagtgc (SEQ ID No. 34) | gcucuacugccccaagugcuu ttcgagaugacggggduucacg (SEQ ID Nos. 75 & 129, respectively) | 21 | 63 | 52.4 | 400 | 1 |
| CK2β14 | aagatccatccgatggcctac (SEQ ID No. 37) | gauccauccgauggccuacuu ttcuagguaggcuaccggaug (SEQ ID Nos. 78 & 130, respectively) | 21 | 62.3 | 42.9 | 571 | 2 |
| CK2β15 | aagactacatccaggacaat (SEQ ID No. 26) | gacuacauccaggacaauuu ttcugauguaggaccugua (SEQ ID Nos. 67 & 131, respectively) | 20 | 52.1 | 38.1 | 80 | 0 |
| CK2β16 | aagactacatccaggacaat (SEQ ID No. 26) | aagacuacauccaggacaauu ttuucugauguaggaccuguu (SEQ ID Nos. 83 & 132, respectively) | 21 | | | | |

TABLE III-continued taget sequences and SiRNA β

| Name | Human target sequence (sense sequence) | SiRNA | Size | Tm | % GC | Position | Hu/mouse homology |
|---|---|---|---|---|---|---|---|
| CK2β17 | aagactacatccaggacaat (SEQ ID No. 26) | ugaagacuacauccaggacuu uuacuucugauguagguccug (SEQ ID Nos. 86 & 133, respectively) | 21 | | | | |

NB: The ATG is in position 341 of the human sequence No. NM_001320.

A subject of the present invention is also a single-stranded oligonucleotide, characterized in that it is defined by the antisense strand or negative strand of the double-stranded oligonucleotide as defined above.

According to an advantageous embodiment of the double-stranded or single-stranded oligonucleotide as defined above, it is stabilized.

Stabilized oligonucleotides are known to those skilled in the art; they can be stabilized in particular by incorporation of modified bases during the in vitro synthesis or by modifications of the bases incorporated beforehand into said oligonucleotides. Examples of these modifications are given in Table IV.

A subject of the present invention is also a precursor of the double-stranded or single-stranded oligo-nucleotide as defined above, characterized in that it is selected from the group consisting of:

a) a single-stranded oligonucleotide corresponding to the sense or antisense strand as defined above, b) a double-stranded oligodeoxynucleotide (DNA) corresponding to the sense and/or antisense strands of the double-stranded oligonucleotide as defined above, c) a hairpin oligoribonucleotide comprising the sequences of the sense and antisense RNA strands as defined above, and d) a double-stranded DNA made up of a sense strand corresponding to the DNA equivalent of the oligo-ribonucleotide defined in c) and of an antisense strand complementary thereto.

For the purpose of the present invention, the expression "DNA equivalent of an RNA sequence" is intended to mean the sequence in which the ribonucleotides (a, g, c, u) of said RNA sequence are replaced with deoxyribonucleotides (a, g, c, t).

The precursors are useful for producing the single-stranded and double-stranded oligonucleotides according to the present invention by the conventional techniques of oligonucleotide synthesis and of transcription using a recombinant vector.

Each of the strands of the siRNA can be synthesized separately and then the complementary strands are hybridized so as to form RNA duplexes. Alternatively, the strands of the siRNA can be synthesized simultaneously.

The siRNA can also be produced in the form of a hairpin RNA molecule according to the principle described in Brummelkamp et al., Science, 2002, 296, 550-553. The hairpin RNA molecule is subsequently cleaved in the cells transfected with said RNA molecule or transduced with an appropriate transcription vector, so as to release the siRNA. This hairpin RNA molecule comprises the sequences of the two strands of the siRNA separated by a short sequence of non-complementary oligo-ribonucleotides of approximately 3 to 12 nucleotides forming a loop of approximately 5 to 15 nucleotides. For example, a loop of approximately 10 nucleotides is formed from a short sequence of approximately 8 ribonucleotides and of two nucleotides derived from the 3' end of the sense strand of the siRNA.

The single-stranded and double-stranded oligo-nucleotides according to the present invention can be either produced by chemical synthesis or by transcription in vitro (test tube) or in cell culture, and then administered in vivo, or they are produced in vivo in the cells of an organism which have been modified with a transcription vector (gene therapy) or a DNA encoding said siRNAs (transgenesis).

The chemical synthesis is carried out according to the conventional phosphoramidite method described in Elbashir et al., Nature, 2001, 411, 494-498. For example, each of the strands of the siRNA can be synthesized according to β-cyanoethyl phosphoramidite chemistry on a solid support using 2'-O-tert-butyl-dimethylsilyl (TBDMS) as a group for protecting the 2'-position of the ribonucleotide. Other protective groups can be used; silyl ether, which protects the 5'-hydroxyl end of the ribonucleotide, can be used in combination with a labile orthoester which protects the 2'-hydroxyl of the ribonucleotide.

The transcription by means of a recombinant vector uses a double-stranded DNA encoding for at least one or the two strands of the siRNA or else a hairpin RNA as defined above. Such DNAs cloned into appropriate expression vectors allow separate or simultaneous transcription of the two complementary strands of said siRNA, as described, respectively, in Sadher et al., Biochem. Int., 1987: 14, 1015 and in European patent EP 0618 966 in the name of Cis Bio International. For example, the method of preparing double-stranded RNA described in European patent EP 0618 966 uses a DNA template attached to a support which allows the simultaneous transcription of the two RNA strands in the form of double-stranded RNA after a step consisting of amplification (PCR) of the target DNA sequence. The double-stranded RNA obtained can be attached to a support and several different siRNA sequences can be analyzed simultaneously.

A subject of the invention is also an expression cassette, characterized in that it comprises at least one precursor as defined above, under the control of appropriate transcriptional regulatory elements, in particular an inducible or non-inducible promoter and a transcription terminator.

A subject of the invention is also a eukaryotic or prokaryotic vector comprising an insert consisting of an oligonucleotide as defined above; preferably, said vector is an expression vector into which an expression cassette as defined above is inserted.

These vectors are constructed and introduced into host cells by conventional recombinant DNA and gene therapy methods, which are known in themselves. Many vectors into which a nucleic acid molecule of interest can be inserted in order to introduce it into and to maintain it in a eukaryotic or prokaryotic host cell are known in themselves; the choice of an appropriate vector depends on the use envisioned for this vector (for example, replication of the sequence of interest, expression of this sequence, maintaining the sequence in extrachromosomal form or else integration into the host's chromosomal material), and also on the nature of the host cell. Use may be made, inter alia, of viral vectors such as adenoviruses, retroviruses, lentiviruses and AAVs into which the sequence of interest has been inserted beforehand, or else nonviral vectors such as plasmids.

Preferably, said vector is a DNA vector (recombinant plasmid or virus) comprising a double-stranded oligodeoxynucleotide as defined above; such a vector encoding an siRNA as defined above is useful for the in vitro or in vivo production of said siRNAs.

Vectors that are particularly suitable for the stable expression of siRNAs are in particular those described in T. R. Brummelkamp et al., Science, 2002, 296, 550-553.

A subject of the present invention is also eukaryotic or prokaryotic cells modified with an oligonucleotide, a precursor, an expression cassette or a vector as defined above.

A subject of the present invention is also a transgenic nonhuman animal, characterized in that it comprises cells modified with an oligonucleotide, a precursor, an expression cassette or a vector as defined above.

A subject of the present invention is also a pharmaceutical composition, characterized in that it comprises at least one oligonucleotide, one precursor or one vector encoding said siRNA, as defined above, and a pharmaceutically acceptable carrier.

Said oligonucleotides (double-stranded oligonucleotide (siRNA), or single-stranded oligonucleotide or precursor of the above), isolated or inserted into a vector as defined above, are introduced into target cells either by passive diffusion, or using physical methods such as electroporation or microinjection, or by associating them with any substance(s) that make(s) it possible to cross the plasma membrane, such as transporters, for instance nanotransporters, liposomes, lipids or cationic polymers, such as calcium phosphate (Sigma kit ref. CA-PHOS), amine (Ambion kit ref. 4502), lipofectamine (Polyplus-transfection kit, ref. 101-05) or fugene-6 (Roche, ref. 1815-091). In addition, these methods can advantageously be combined, for example using electroporation combined with liposomes.

In certain cases, it is not necessary to associate the oligonucleotides according to the invention with a substance allowing them to pass through the plasma membrane, insofar as the siRNAs are small enough to diffuse freely in the various cell compartments. They can act in the cytoplasm, but also at the nuclear membrane, or even in the nucleus.

According to an advantageous embodiment of said composition, said oligonucleotide, said precursor or said vector are associated with at least one substance that makes it possible to cross the plasma membrane, such as transporters, for instance nanotransporters, liposomes, lipids or cationic polymers.

According to another advantageous embodiment of said composition, said oligonucleotide, said precursor or said vector is associated with at least one substance that allows targeting into specific cells, tissues or organs, such as antibodies and peptides, in particular peptides capable of crossing the blood-brain barrier, for instance the Pep:Trans™ peptides. Other peptides can advantageously be used to facilitate the transfection of siRNA through the plasma membrane of cells; the antibodies described in Lu Z. R. et al. (Nature Biotechnol., 1999, 17, 1101-1104) can in particular be used for targeting cancer cells.

According to yet another advantageous embodiment of said composition, said oligonucleotide, said precursor or said vector is combined with at least one antiviral or anticancer agent.

According to another advantageous embodiment of said composition, it comprises a mixture of several oligonucleotides or of their precursors, or else one or more expression vectors for said mixture of oligonucleotides, and in particular a mixture comprising at least one oligonucleotide specific for the α subunit, at least one oligonucleotide specific for the α' subunit and at least one oligonucleotide specific for the β subunit.

A subject of the present invention is also the use of an oligonucleotide, of a precursor or of a vector as defined above, for preparing a medicinal product for use in the prevention and/or treatment of cancer.

A subject of the present invention is also the use of a oligonucleotide, of a precursor or of a vector as defined above, for preparing a medicinal product for use in the prevention and/or treatment of viral diseases.

A subject of the present invention is also a product containing at least one oligonucleotide, one precursor or one vector as defined above and an anticancer active ingredient, as a combined preparation for simultaneous, separate or sequential use, in the prevention and/or treatment of cancer.

A subject of the present invention is also a product containing at least one oligonucleotide, one precursor or one vector as defined above and an antiviral active ingredient, as a combined preparation for simultaneous, separate or sequential use, in the prevention and/or treatment of viral diseases.

The useful dosage varies according to the condition to be treated, to the route and rate of administration, and to the nature and the weight of the species to be treated (human or animal). The oligonucleotides are used by digestive (oral, sublingual), parenteral or local administration. They may be in the form of simple or sugar-coated tablets, of gelatine capsules, of granules, of a syrup, of suppositories, of injectable preparations, of ointments, of creams, of gels or of an aerosol, which are prepared according to the usual methods. In these pharmaceutical forms, the oligonucleotides are incorporated into excipients normally used in pharmaceutical compositions, such as talc, gum arabic, lactose, starch, magnesium stearate, cocoa butter, aqueous or nonaqueous carriers, fatty substances of animal or plant origin, paraffin derivatives, glycols, various wetting, dispersing or emulsifying agents, or preserving agents.

In vitro, the concentrations that can be used in rats are between 10 nM and 200 μM; the in vivo doses can therefore be between 1 μg and 20 mg/kg. The corresponding doses in humans can be deduced from this information.

A subject of the invention is also the use of an oligonucleotide, of a precursor, of a vector, of modified eukaryotic or prokaryotic cells or of a transgenic animal, as defined above, for screening for molecules capable of selectively modulating the activity of the α, α' or β subunits of the CK2 protein; for example, it is possible to specifically inhibit the expression of one of the subunits in vivo or in vitro and thus to screen for molecules that are active on the other subunit; such molecules represent potential medicinal products that are useful for the prevention and treatment of pathologies related to a deregulation (increase or decrease) in the activity of the CK2 protein kinase in cells.

By way of example of a pathology related to a deregulation of CK2 activity, mention may be made of male infertility due to an absence of CK2 α' with no compensation by α which is absent in the germ cells at the final stage of spermatogonia differentiation (Xu et al., Nature Gen., 1999, 23, 118-121).

Compared with the antisense oligonucleotides of the prior art, the oligonucleotides, and in particular the siRNAs, according to the invention have the following advantages:
- they are stable in vitro and in vivo,
- they are active at low concentrations (of the order of 20 nM in vitro) and inhibit very effectively (>80% inhibition) the expression and, consequently, the activity of the CK2 protein kinase in cells,
- they have a prolonged effect, up to 6 days.

Figure 2:
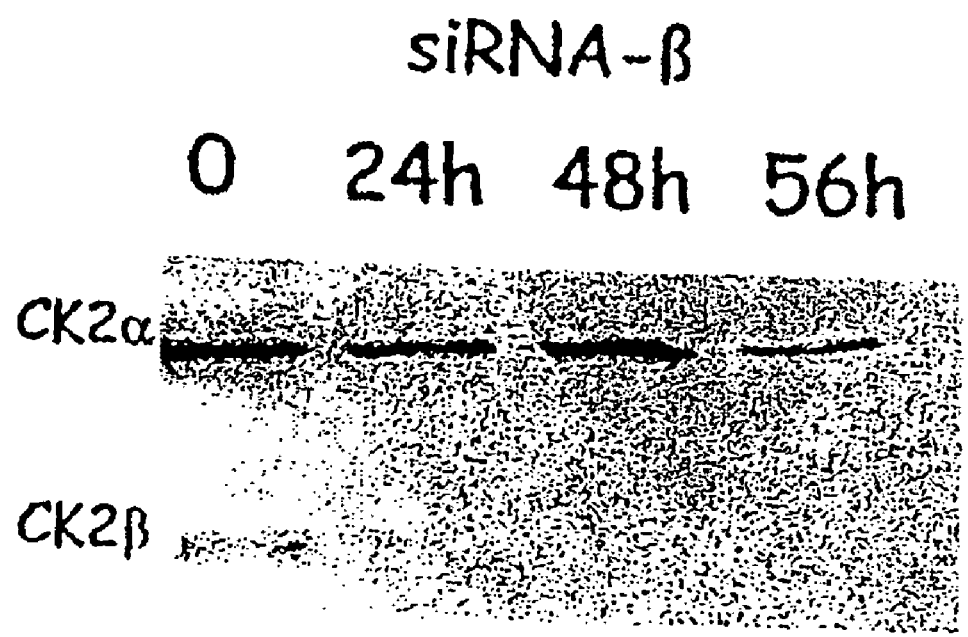
Figure 3:
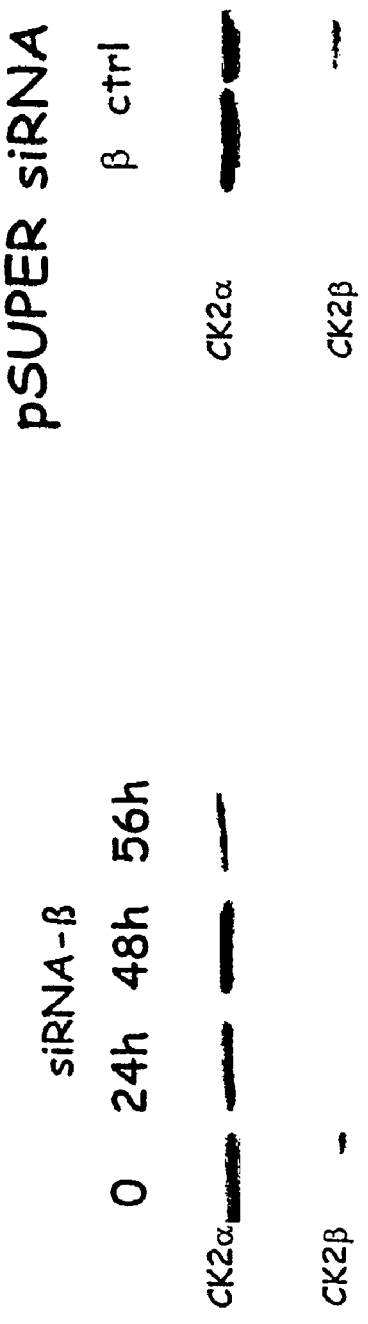
Figure 4:
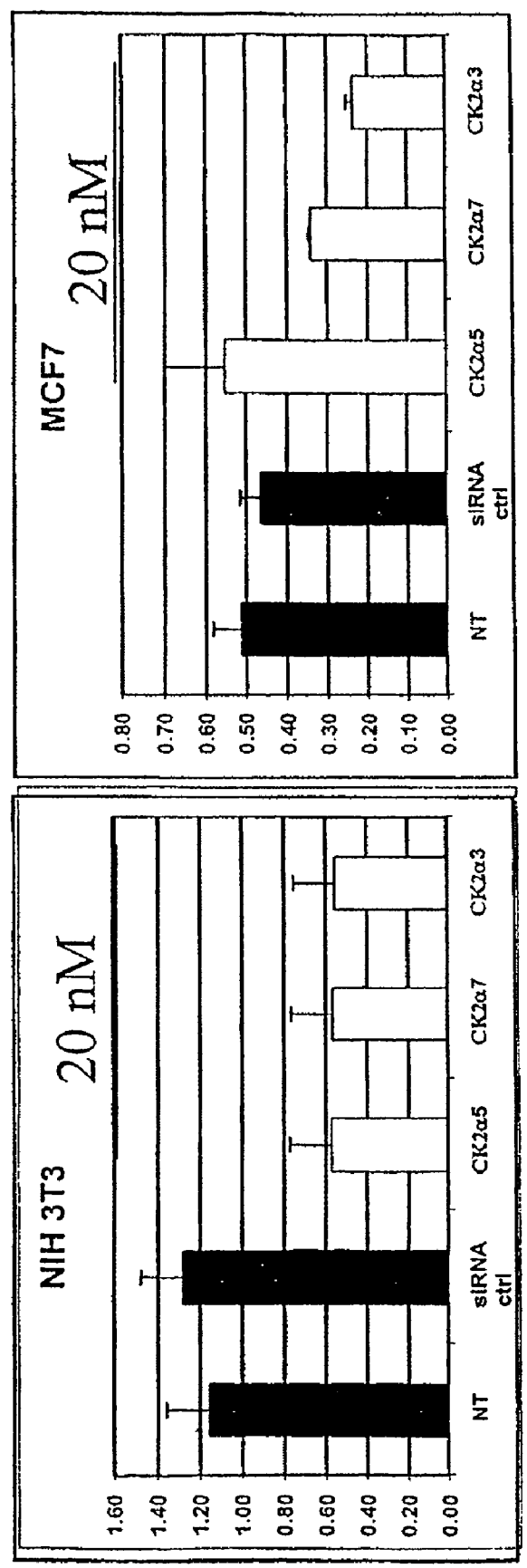

Besides the above arrangements, the invention also comprises other arrangements which will emerge from the description which follows, which refers to examples of use of the siRNA corresponding to the sequence SEQ ID No. 26 according to the present invention and also to the attached drawings in which:

FIG. 1 illustrates the immunofluorescence analysis of the inhibition of the expression of the CK2 protein kinase β subunit by an siRNA targeting the sequence SEQ ID No. 26 (psi); the cells are labeled with an anti-CK2β primary antibody and a fluorescein-coupled secondary antibody (green fluorescence), and then counter stained with propidium iodide (red fluorescence). The inhibition is measured by the ratio of the number of CK2β-positive cells (green fluorescence) to the total number of cells (red fluorescence). The values represent the means of two independent measurements±SEM. A final concentration of 100 nM of siRNA inhibits 90% of the expression of the CK2 protein kinase β subunit;

FIG. 2 illustrates the kinetics of inhibition of the expression of the CK2 protein kinase β subunit in the presence of a synthetic siRNA (siRNA-β) targeting the sequence SEQ ID No. 26;

FIG. 3 illustrates the comparative analysis of the inhibition of the expression of the CK2 protein kinase β subunit by a synthetic siRNA CK2β (sense sequence SEQ ID No. 83 and antisense sequence SEQ ID No. 84) or an siRNA CK2β expressed in the target cells by means of a recombinant vector (pSUPERsiRNA) producing a hairpin RNA (SEQ ID No. 85) corresponding to the siRNA of sense sequence SEQ ID No. 86 and antisense sequence SEQ ID No. 87;

FIG. 4 illustrates the improvement in the siRNA sequences. Human cells (MCF7 line) and murine cells (NIH 3T3 line) were transfected with various siRNAs targeting the α subunit (CK2α3, CK2α7, CK2α5) and possibly exhibiting mismatches with the target RNA, and a control siRNA (ctrl). The cells were labeled with an anti-CK2α primary antibody and a fluorescein-coupled secondary antibody (green fluorescence), then counter stained with propidium iodide (red fluorescence). The inhibition of the expression of the α subunit is measured by the ratio of the number of CK2α-positive cells (green fluorescence) to the total number of cells (red fluorescence).

EXAMPLE 1

Expression of an Oligoribonucleotide According to the Invention in Target Cells Modified with a Recombinant Vector a) A DNA sequence (gatcccctgaagactacatccaggacttcaagag agtcctggatgtagtcttcatttttggaaa, SEQ ID No. 82) was cloned into the vector pSUPER according to the conditions described in Brummelkamp T R et al. (Science, 2002, 296, 5567, 550-3). The recombinant vector thus obtained (pSUPER siRNA) allows the expression of an siRNA-β or CK2β targeting the sequence SEQ ID No. 26, from a hairpin transcript (FIG. 3).

b) NIH 3T3 cells are transfected with the vectors obtained in a) according to a transfection protocol using Fugene 6 (Roche).

EXAMPLE 2

Preparation of Synthetic Ologoribonucleotides that are Optionally Stabilized a) The two RNA strands are synthesized according to known methods (RNA phosphoramidine method, see in particular Elbashir S. M. et al., Nature, 2001, 411, 494-498).

b) In order to stabilize them, it is advantageous to modify them by inserting modified nucleotides into the two RNA strands, during the in vitro synthesis.

Table IV below illustrates examples of modified nucleotides.

| Modified nucleotide | First application | Second application |
|---|---|---|
| 2'F-CTP | Resistance to nuclease | |
| 2'F-UTP | Resistance to nuclease | |
| 2'NH$_2$-CTP | Resistance to nuclease | |
| 2'NH$_2$-UTP | Resistance to nuclease | |
| 2'N$_3$-CTP | Resistance to nuclease | Post-synthesis modification |
| 2'N$_3$-UTP | Resistance to nuclease | Post-synthesis modification |
| 2-thio CTP | UV-crosslinking | |
| 2-thio UTP | Modified hybridization | UV-crosslinking |
| 4-thio UTP | Modified hybridization | UV-crosslinking |
| 5-iodo CTP | UV-crosslinking | |
| 5-iodo UTP | UV-crosslinking | |
| 5-bromo UTP | UV-crosslinking | |
| 2-chloro ATP | UV-crosslinking | |
| Adenosine 5'-(1-thiotriphosphate) | Chemically unstable | Resistance to nuclease |
| Cytidine 5'-(1-thiotriphosphate) | Chemically unstable | Resistance to nuclease |
| Guanosine-5'-(1-thiotriphosphate) | Chemically unstable | Resistance to nuclease |
| Uridine-5'-(1-thiotriphosphate) | Chemically unstable | Resistance to nuclease |
| Pseudo-UTP | | |
| 5-(3-aminoallyl)-UTP | Post-synthesis modification | |
| 5-(3-aminoallyl)-dUTP | Post-synthesis modification | |

Such nucleotides are in particular available from Ambion.

EXAMPLE 3

Inhibition of the Expression of the CK2 Protein Kinase β Subunit by Synthetic siRNA 3T3 fibroblasts were cultured in a drop of 5 μl (2000 cells) in complete culture medium, in the wells of an immunofluorescence slide (40 wells 2 mm in diameter; super teflon slide, reference 74890.01 (Prolabo)). The 3T3 cells were transfected using the siport® transfection kit (Ambion), with a final concentration of 5, 20, 50 or 100 nM of siRNA targeting the sequence SEQ ID No. 26, in a volume of 5 μl, or were nontransfected, and then the cells were incubated for 2 days at 37° C. The cells were subsequently washed and fixed with a paraformaldehyde solution (4% in PBS). The cells were subsequently stained with propidium iodide and labeled using a primary antibody against the CK2 protein β subunit (βc antibodies; Filhol et al. 1994 Biochem Biophys Res Commun. 198 660-5) and a secondary antibody coupled to a fluorophor, such as cyanamide 3. The fluorescence was analyzed using a scanner (Genomic Solution) and the inhibition of expression of the CK2 protein kinase was expressed by the ratio of the number of cells expressing the CK2 protein kinase (red cells labeled with the βc antibodies) to the total number of cells (blue cells labeled with propidium iodide).

The results are given in FIG. 1 and show that a concentration of 20 nM of siRNA inhibits 90% of the expression of the CK2 protein kinase β subunit.

EXAMPLE 4

Study of the Inhibition of the Expression of β CK2 by Synthetic siRNA or an siRNA Produced in the Target Cells Modified with an Expression Vector NIH 3T3 cells transfected either with an siRNA-β targeting the sequence SEQ ID No. 26 (20 nM) or with the corresponding expression vector (pSUPER siRNA) are cultured for the periods indicated in FIG. 2. After washing in PBS, they are lysed in a TDG buffer (10 mM Tris, HCl, pH 7.4, 0.1% glycerol, 1 mM DTT, 500 mM NaCl, 0.1% Triton X-100) and centrifuged for 15 min at 15 000 g at 4° C. The supernatant is assayed for its protein content and 40 μg are analyzed by SDS-PAGE. The proteins are then transferred onto a PVDF membrane.

After saturation of the membrane in PBS containing 0.05% Tween 20 and 3% BSA for 1 hour, the CK2β subunit is visualized with the PC antibody.

An inhibition of the expression of the CK2 protein β subunit is observed with the synthetic siRNA or the siRNA produced by an expression vector (FIG. 3); this inhibition is observed from 24 h, as shown by the inhibition kinetics with the synthetic siRNA (FIGS. 2 and 3).

EXAMPLE 5

Improvement in the siRNA Sequences

The inhibition of the expression of the human or murine CK2 protein α subunit by various siRNAs (CK2α3, CK2α7, CK2α5) exhibiting or not exhibiting mismatches with the target RNA was analyzed by immunofluorescence as described in example 3. The siRNAs are specific for the murine transcript and exhibit 0 (CK2α3), 1 (CK2α7) or 2 (CK2α5) mismatch(es) with the human transcript (Table I); for α7, the mismatch is in the 5' portion of the target sequence, whereas, for α5, the mismatch is in the 3' portion of the target sequence.

Human cells (MCF7 line) and murine cells (NIH 3T3 line) were transfected with various siRNAs targeting the a subunit (CK2α3, CK2α7, CK2α5) or with a control siRNA (ctrl). The cells were labeled with an anti-CK2a primary antibody and a fluorescein-coupled secondary antibody (green fluorescence), and then counter stained with propidium iodide (red fluorescence). The inhibition of the expression of the α subunit was measured by the ratio of the number of CK2α-positive cells (green fluorescence) to the total number of cells (red fluorescence).

The results show that the presence of any mismatch with the target RNA decreases the effectiveness of the siRNAs (FIG. 4; see α5 in the human line compared with the murine line).

As emerges from the above, the invention is in no way limited to those of its methods of implementation, execution and application which have just been described more explicitly; on the contrary, it encompasses all the variants thereof that may occur to those skilled in the art, without departing from the context or the scope of the present invention.

The invention claimed is:

1. A double-stranded oligonucleotide comprising two strands of 19 to 23 nucleotides, each strand consisting, from 5' to 3', of a sequence of 17 to 21 ribonucleotides and two deoxyribo- or ribonucleotides, the 17 to 21 ribonucleotide RNA sequences of said strands being complementary and the two nucleotides of the 3' ends being protruding, wherein the RNA sequence of the sense strand or positive strand is selected from the group consisting of a 17 to 21 ribonucleotide fragment of a transcript of a protein kinase CK2 beta-subunit which is included between positions 80-100, from the ATG codon, with reference to the human transcript sequence SEQ ID NO: 90, and a 17 to 21 ribonucleotide fragment having at least 80% identity with the preceding fragment, wherein the sequence of the sense strand or positive strand is selected from the group consisting of the sequences SEQ ID NO: 67, 83 and 86, and wherein the double-stranded oligonucleotide inhibits specifically more than 80% of the expression of the protein kinase CK2 beta-subunit and of the corresponding mRNA in human cell culture at a concentration of between 1 and 200 nM.

2. The double-stranded oligonucleotide as claimed in claim 1, wherein each of the strands further comprises a phosphate group in the 5' position and a hydroxyl group in the 3' position.

3. The double-stranded oligonucleotide as claimed in claim 1, wherein said two protruding nucleotides of the 3' ends are identical.

4. The oligonucleotide as claimed in claim 1, which is a stabilized oligonucleotide.

5. A single-stranded oligonucleotide consisting of the antisense strand or negative strand of the double-stranded oligonucleotide as claimed in claim 3.

6. A hairpin oligoribonucleotide comprising the sense and antisense strands of the double-stranded oligoribonucleotide as claimed in claim 1 with two ribonucleotides at their 3' ends.

7. A product containing at least one oligoribonucleotide as claimed in claim 1, and an antiviral active ingredient, as a combined preparation for simultaneous, separate or sequential use, in the treatment of viral diseases.

8. A product containing at least one oligonucleotide as claimed in claim 1, and an anticancer active ingredient, as a combined preparation for simultaneous, separate or sequential use, in the treatment of cancer.

9. A cassette for the expression of a siRNA or a hairpin RNA, comprising an isolated DNA sequence consisting of a DNA sequence encoding (i) the sense or antisense strand or both strands of the oligoribonucleotide as claimed in claim 1 or (ii) an hairpin RNA comprising the sense and antisense strands of said oligoribonucleotide with two ribonucleotides at their 3' ends, wherein said DNA sequence is operably linked to an inducible or noninducible promoter and a transcription terminator.

10. A vector for the expression of a siRNA or a hairpin RNA, comprising an isolated DNA sequence consisting of a DNA sequence encoding (i) the sense or antisense strand or both strands of the oligoribonucleotide as claimed in claim 1 or (ii) an hairpin RNA comprising the sense and antisense strands of said oligoribonucleotide with two ribonucleotides at their 3' ends.

11. A eukaryotic or prokaryotic cell, wherein the eukaryotic or prokaryotic cell is modified with oligonucleotide as claimed in claim 1.

12. A pharmaceutical composition, comprising at least one oligonucleotide as claimed in claim 1, one hairpin RNA comprising the sense and antisense strands of said oligoribonucleotide with two ribonucleotides at their 3' ends or one expression vector thereof comprising an isolated DNA sequence consisting of a DNA sequence encoding said oligoribonucleotide or hairpin RNA.

13. The pharmaceutical composition as claimed in claim 12, wherein said oligonucleotide, hairpin RNA or vector is associated with at least one substance that makes it possible to cross the plasma membrane.

14. The pharmaceutical composition as claimed in claim 12, wherein said oligonucleotide, hairpin RNA or vector is associated with at least one substance that allows targeting into cells, tissues or organs.

15. The pharmaceutical composition as claimed in claim 12, wherein said oligonucleotide, hairpin RNA or vector is combined with at least one antiviral or anticancer agent.

16. The pharmaceutical composition as claimed in claim 12, comprising a mixture of several oligonucleotides or hairpin RNA, or else one or more expression vectors for said mixture of oligonucleotides or hairpin RNA.

17. The pharmaceutical composition as claimed in claim 12, comprising a mixture of at least one oligonucleotide specific for a protein kinase CK2 alpha-subunit, at least one oligonucleotide specific for a protein kinase CK2 alpha'-subunit and at least one oligonucleotide specific for a protein kinase CK2 beta-subunit.

* * * * *